United States Patent [19]

Strelioff et al.

[11] 4,036,065
[45] July 19, 1977

[54] GRAIN LOSS MONITOR

[75] Inventors: William P. Strelioff; William S. Elliott; Dale Johnson, all of Saskatoon, Canada

[73] Assignee: Senstek Ltd., Saskatoon, Canada

[21] Appl. No.: 685,282

[22] Filed: May 11, 1976

[51] Int. Cl.² .......................................... G01N 29/00
[52] U.S. Cl. ..................................... 73/432 R; 73/552
[58] Field of Search ................. 73/432 R, 194 B, 552; 324/71 CP

[56] References Cited

U.S. PATENT DOCUMENTS 3,540,454 11/1970 Giebelstein ..................... 73/432 R X

FOREIGN PATENT DOCUMENTS 1,810,519 11/1968 Germany ........................... 73/194 B Primary Examiner—Richard C. Queisser
Assistant Examiner—Joseph W. Roskos
Attorney, Agent, or Firm—Stanley G. Ade

[57] ABSTRACT

A percentage of the grain lost is sampled constantly by sensors at locations across the rear of the sieve of a combine and the sound of the grain kernels striking the sensors is picked up by a microphone, amplified, filtered and fed to a ratio computing device which calculates the total grain loss from the sampling and displays same on a meter. A further sensor samples grain passing through the rear portion of a straw walker of a combine as this bears a direct relationship to the quantity of grain passing over the end of the walker. It can therefore be used to calculate the grain loss over the end of the walker. Once again the sound of the grain kernels striking the sensor is picked up by a microphone, amplified, filtered and fed to a ratio computing device which calculates the grain loss over the end of the walker and displays same on the meter. A switching device enables the total of the grain losses to be calculated from the two sensors by means of a summation device to which both sensor signals are connected. This switching device also enables the operator to weed out the grain loss over the sieve or the grain loss over the walker thus enabling him to determine where adjustments are required.

11 Claims, 9 Drawing Figures

GRAIN LOSS MONITOR

BACKGROUND OF THE INVENTION

This invention relates to combine harvesters and the like and more particularly to a device for monitoring the grain loss during the harvesting operation.

A combine harvester or similar machine used to harvest grain is provided with means to vary the ground speed so that different crop conditions may be accommodated. There are many factors affecting the harvesting of the crop such as varying moisture content, varying quantity of grain and straw, the height of the crop and the general quality of the grain.

Each combine machine, of course, has an ideal operating speed for any particular crop condition and this speed is determined by the feed rate, the conveyor rate, the concave width and the straw walker assembly design.

At one particular ground speed, the combine is capable of recovering the highest percentage of grain for that particular crop condition under which it is operating and this speed is normally determined by an operator who, depending upon his experience, visually judges the crop conditions and knows the various adjustments and capabilities of his machine.

However, it will be appreciated that crop conditions can vary widely in the same field so that it is necessary for the operator to constantly vary the speed of his machine in order to attempt to maintain the machine at the most efficient groundspeed.

One method of measuring the efficiency of the machine under certain conditions, is to measure the amount of grain lost over the back of the sieve component and over the straw walker assembly. Such devices, however, suffer from the inability to distinguish grain from other threshed crop materials such as heads, chaff, straw and the like.

SUMMARY OF THE INVENTION

The present invention has several objects in view in order to enable the operator to control his machine so that the grain loss is minimal thereby ensuring that the harvesting is proceeding most efficiently.

One of the principal objects of the present device is to provide a monitoring device which constantly samples a percentage of the grain passing over the rear of the sieve and automatically translates this to display the total amount of grain being lost at this particular location. Obviously, it would be desirable to measure the entire quantity of grain passing over the rear of the sieve, but this is not practical so that the sampling method is utilized.

Another object is to sample the amount of grain passing over the straw walkers and in this regard, a unique approach is used. The loss sensing of grain over the straw walker assembly is more difficult than measuring the grain passing over the rear of a sieve component because putting a sensor into the flow of straw obstructs the straw and may cause blockage to occur.

As the grain-straw mixture is fed into the front of the straw walker, separation commences. It has been found that the majority of grain is separated at the front end of the straw walker assembly and as the mixture of grain and straw proceeds to the rear end of the assembly, the amount of grain coming out of the mixture decreases. This is apparent because as the mixture proceeds to the rear, it contains a lesser amount of grain but the quantity of straw remains constant.

Tests on straw walkers have shown that the amount of grain lost over the end of the straw walker is approximately equal to the amount of grain separated in the last 18 inches of the straw walker. Therefore, by sensing the amount of grain that is separated in the last 18 inches of the walker, an indication is given of how much is being lost and although this 18 inches distance varies with the amount of material being combined and the weight ratio of grain to straw, nevertheless when operating at capacity, this length remains relatively constant and can be used to give an indication of the grain loss over the end of the straw walker without interfering with the flow of straw thereover.

Both of the sensors used in the present apparatus utilize the sound of grain impinging upon a sensing device thereby constantly sampling a percentage of the grain passing over the sieve components or being separated by the rear portion of the straw walker assembly.

Insofar as the sieve component is concerned, a plurality sensing fingers depend from a common support tube in spaced relationship and the sound of the grain impinging upon these sensing fingers, is transmitted to the tube and through a column of air therein, to an electrical transducer at one end thereof whereupon the sounds are amplified, thereby forming pulses which in turn are fed through a band-pass filter, transferred to square wave pulses and then connected to a measuring circuit. At this point, the measuring circuit multiplies the pulses by a pre-determined figure in order to calculate 100% of the grain of which a small percentage has been sampled. This is then displayed on a convenient meter so that the operator knows at all times the quantity of grain passing over the rear of the sieve component.

The transducer measuring the amount of grain separated in the last portion of the straw walker is also detected and sensed by an electrical transducer and is fed through similar circuitry to be displayed upon the same display means or meter, one or the other being selected by means of a convenient switch.

However, another object of the invention is to provide means whereby the amount of grain passing over the sieve component and the amount of grain separated by the straw walker assembly can be added together to display a total amount of grain being lost during the combining operation at any one time.

As an example, the operator can tell at all times the total amount of grain being lost, but if it exceeds a pre-determined amount, he can select the read-out from the monitoring of the sieve component or the read-out giving the monitoring of the straw walker assembly and may thus ascertain where the excess grain is being lost and make the necessary adjustments in order to correct the situation.

Another object of the invention is to provide a device of the character herewithin described which is extremely simple in construction and can be readily fitted to an existing combine without interfering with the operation thereof. Furthermore, the read-out device can be situated conveniently to the operator so that at all times he can obtain information as to the grain loss situation, the sampling being done on a continuous percentage basis.

With the foregoing objects in view, and other such objects and advantages as will become apparent to those skilled in the art to which this invention relates as

DESCRIPTION OF THE DRAWINGS

In the drawings like characters of reference indicate corresponding parts in the different figures.

DETAILED DESCRIPTION

One of the problems in measuring grain loss over a sieve component is that it is difficult to determine exactly how the grain is leaving the sieve and in what direction it is travelling. The problem is further compounded when going up and down hills or on a side hill and when varying combine settings for speed, sieve openings and the like.

Under these circumstances, a conventional pad sensor can give false loss readings for the simple reason that the percentage of the total grain that hits the pad depends on the direction of the grain off the end of the sieve and the position of the pad sensor.

As mentioned previously, straw walker sensing is much more difficult because normally a sensor cannot be placed in the flow of straw otherwise it causes an obstruction.

Figure 7:
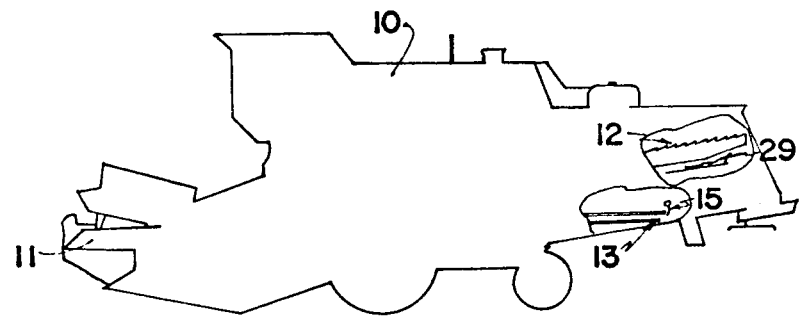
FIG. 7 is a schematic side elevation of a typical combine with the sides broken away to show the approximate location of the two grain loss monitors.

Proceeding therefore to describe the invention in detail, reference should first be made to FIG. 7 in which 10 illustrates schematically a combine having an intake end 11, a straw walker assembly collectively designated 12 and a sieve component collectively designated 13, all of which are conventional.

At the rear end 14 of the sieve component 13 there is provided a constant percentage sensor device collectively designated 15.

In this particular embodiment, it incorporates a pick-up and support tube 16 having closed ends and extending between the side wall supports 17 of the combine immediately above the rear end 14 of the sieve. This tube 16 is preferably made of a rigid plastic material and incorporates a column of air therein (not illustrated).

Figure 3:
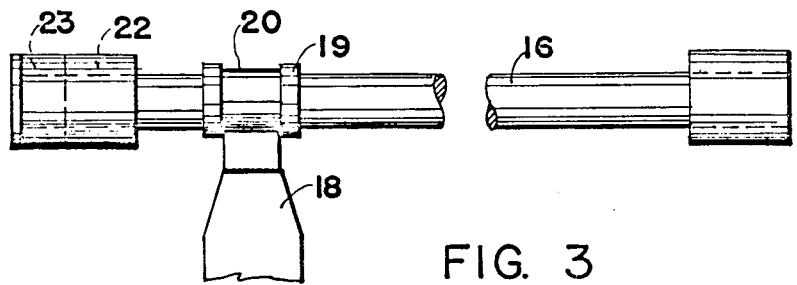
FIG. 3 is an enlarged front elevation of the grain loss monitor for the sieve component.
Figure 4:
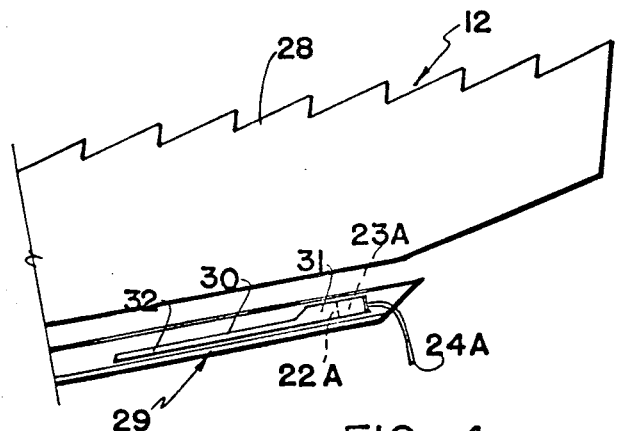
FIG. 4 is a schematic view of part of a walker assembly showing the grain loss monitor situated beneath the walker deck.
Figures 5, 6:
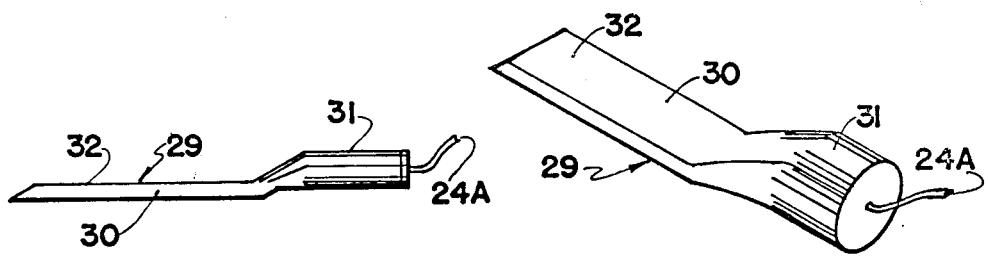
FIG. 5 is an enlarged side elevation of the grain loss monitor of FIG. 4.
FIG. 6 is an isometric view of FIG. 5.

A plurality of vertical situated sensor fingers 18 are secured in spaced relationship along the length of the tube 16 and depending downwardly therefrom. Various ways can be used to attach the fingers to the wall of the tube 16 and one such method is shown in FIG. 3 in which collars 19 engage around the wall of the tube 16 and each sensing finger includes a sleeve 20 engaged around the wall of the tube 16 between collars 19 and these collars and sleeve may either be adhesively secured to the tube or may form part of the tube by screw threaded connections one with the other (not illustrated).

Figures 1, 2:
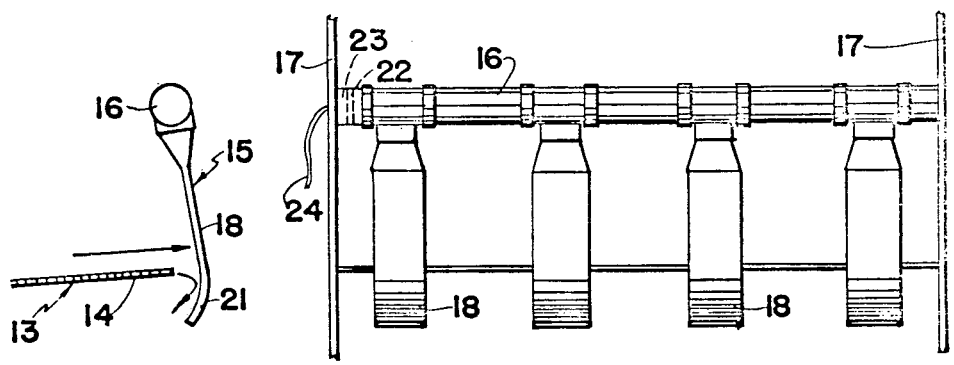
FIG. 1 is a side elevation of the grain loss monitoring device situated at the rear end of a sieve component which is shown schematically.
FIG. 2 is an end view of FIG. 1.

The sensing fingers 18 are also preferably made from a rigid plastic material and it will be noted, upon reference to FIG. 1, that the lower end portions 21 of the fingers curve slightly towards the rear end of the sieve component 13 and are in the form of relatively flat strips.

The positioning of these fingers is such that any grain passing over the end of the sieve 13, in the area of the fingers 18, impinges upon these fingers which are held rigidly in position by the mounting of the tube between the supports 17 by any convenient means.

It will therefore be appreciated that a constant percentage sampling of grain is taking place at this particular location.

As an example, if the sieve component is 40 inches wide and four strip sensors 18 are provided with an effective width of 7.2 inches then 18% of the total lost grain over the end of the sieve component is being sampled.

Figure 8:
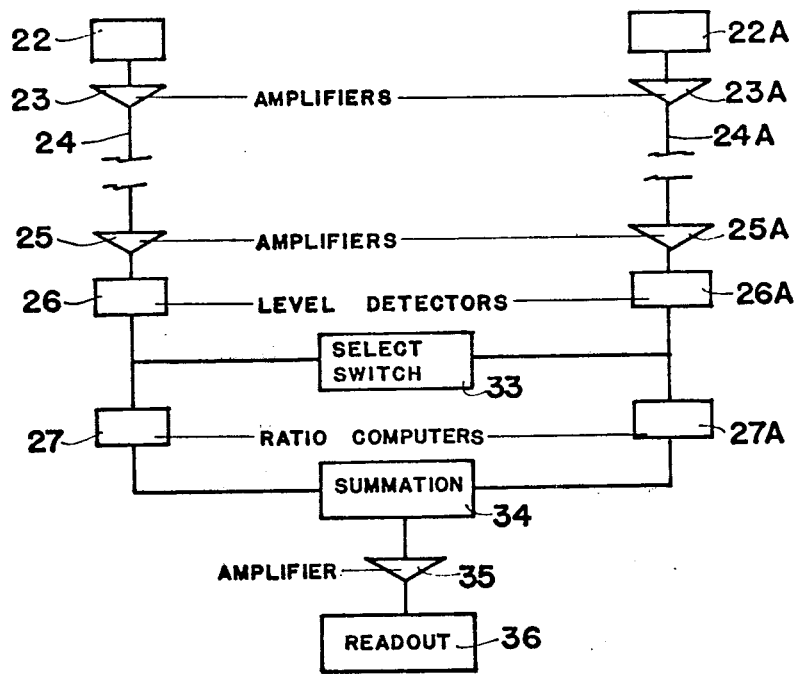
FIG. 8 is a schematic block diagram of the electrical circuit of the entire monitor system.

An electric transducer in the form of a microphone (indicated schematically be reference character 22) is situated within one end of the tube 16 together with a conventional amplifier shown schematically by reference character 23 in FIG. 8.

The amplifier 23 is required because the level of electrical signal produced by sound transducer 22 is too low and may be degraded by electrical pickup in the long lines from the rear of the combine to the instrument which is normally situated at the front of the combine. The sound of the grain impinging upon strips 18 is transmitted to the wall of the tube and thence through the air column within the tube, to the transducer 22 so that the total tube area or volume is being monitored by this transducer regardless of the origin of the sound.

Figure 9:
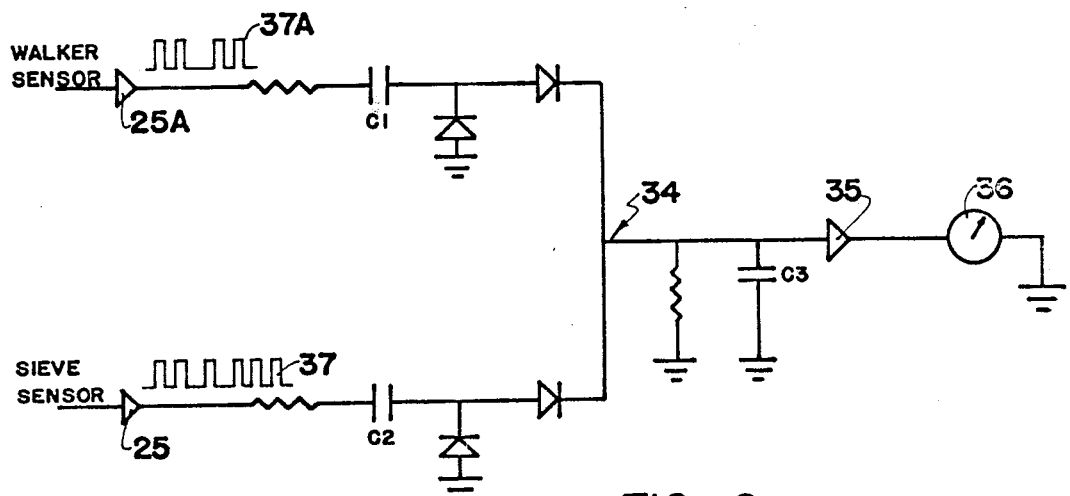
FIG. 9 is a wiring diagram of the ratio computer circuit forming part of the schematic circuitry of FIG. 8.

The sound transducer 22 and amplifier 23 (which is conventional) develop voltage spikes which are transmitted from the amplifier 23 via conductor cable 24 to the electronic circuitry shown in FIGS. 8 and 9, and which may be situated within a convenient package (not illustrated) in the cab of the combine.

A further amplifier 25 modifies the pulses and a level detector 26, screens out unwanted pulses by means of band-pass filters and includes a pulse generating circuit responsive to the detected voltage spikes, to generate square wave pulses. All of this electrical circuitry is conventional and it is not believed necessary to describe same further.

A ratio computer 27 is provided and shown in detail in FIG. 9 which will hereinafter be described.

Situated below the deck 28 of the straw walker assembly 12, is a straw walker sensor collectively designated 29. This extends longitudinally under approximately the last 18 inches of the deck and is preferably positioned centrally between the two sides. It includes a flat strip-like portion 30 upon one end of which is formed a substantially cylindrical portion 31 and a sound transducer 22A is situated within this portion 31 together with an amplifier 23A, both of which are similar to components 22 and 23 hereinbefore described.

This sensor 29 is also hollow and operates in a manner similar to sensor 15. It is preferably manufactured from a rigid plastic material and grain impinging upon the upper surface 32, is transmitted via the air column therein, to the transducer 22A and amplified by the amplifier 23A, it being understood that the sensor 29 is closed ended.

A cable or conductor 24A conveys the generated pulses to the electronic section and amplifier 25A is provided to amplify the pulses at this point. A level detector 26A similar to level detector 26, is also provided together with a ratio computer 27A, all of which act in a similar manner to the components hereinbefore described.

A selector switch 33 is provided enabling either the square wave pulses from the sieve sensor 15 or the square wave pulses from the straw walker sensor 29, to be fed to a further amplifier 34. The switch 33 also permits the feeds from both sensors to be added together by means of summation circuitry 34A. The signals are fed to amplifier 35 and thence to a read-out device 36 which may take the form of a meter suitably calibrated.

Summarizing, therefore, sensors 15 and 29 monitor a constant percentage reading of the total loss at the locations of the sensors. The electronics then determine what percentage of the total loss is being monitored and multiply the outputs from the sieve and walker sensors by the correct factor and displays this total loss on the meter or read-out device 36. Switch 33 allows the operator to monitor the loss from the walkers and the sieve separately to accurately determine the location and amount of the loss.

As mentioned previously, the ratio computer circuitry is shown in FIG. 9 which includes capacitors C1 and C2 receiving the feeds from amplifiers 25 and 25A. The amount of charge in capacitors C1 and C2 is proportional to the capacitors' value. Therefore, selecting the capacitors C1 and C2 in the correct ratio, determines what contribution each will have to the voltage on capacitor C3 for a certain input frequency. This, therefore, takes into account the sampling percentage of each of the sensors.

Reference characters 37 and 37A in FIG. 9 indicate schematically, typical square wave pulses which might be received in both of the circuits.

Referring back to the selector switch 33, this switch is usually in the position to connect both feeds to the summation circuitry 34A, but if one or the other sensors is required, then the selector switch 33 shorts out the sensor not required thus letting the other signal pass through to the read-out or meter 36.

Since various modifications can be made in our invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

What we claim as our invention is:

1. A grain loss monitor device for combines and the like which includes a sieve component and a straw walker assembly for separating threshed grain from straw, chaff and the like; comprising in combination a sensor component situated adjacent the rear end of the sieve component, said sensor component including pick-up and support means spanning said sieve component adjacent the rear end thereof and spaced above said rear end, and a plurality of substantially vertical sensing fingers secured to said pick-up and support means and depending therefrom in spaced relationship across the rear end of the sieve component, said fingers extending downwardly from said pick-up and support means to adjacent the rear end of said sieve component whereby a constant percentage of grain passing over said sieve component impinges upon said fingers, electrical transducer means in said pick-up and support means responsive to said impingement of grain, electrical amplifying means operatively connected to said transducer means and detector means operatively connected to said amplifying means, said detector means detecting a range of amplitudes of voltage spikes above a pre-determined amplitude, the range of amplitudes including voltage spikes developed from said grain impingement, a pulse generating circuit connected to the amplitude detecting circuit and responsive to the detected voltage spikes to generate square wave pulses and a measuring circuit connected to said pulse generating circuit.

2. The device according to claim 1 in which said measuring circuit includes computing means to compute the total grain loss over said sieve from the constant percentage sampled by said device and indicating means operatively connected to said measuring circuit.

3. The device according to claim 1 in which said pick-up and support means comprises a hollow, closed-ended tube having a column of air therewithin, said transducer means and said amplifying means being situated at one end of said tube, said sensing fingers being operatively connected to the wall of said tube whereby the sounds of grain impinging upon said fingers is transmitted via said fingers to the wall of said tube and via said column of air to said electrical transducer means.

4. The device according to claim 1 which includes a further grain loss sensor component including a sensor tube situated below said straw walker assembly adjacent the rear portion thereof whereby a percentage of grain separated by said rear portion impinges upon said further sensor tube, electrical transducer means in said further sensor tube, responsive to the impingement of grain upon said further sensor means, electrical amplifying means operatively connected to said last mentioned transducer means, and means operatively connecting said last mentioned amplifying means to said pulse generating circuit.

5. The device according to claim 2 which includes a further grain loss sensor component including a sensor tube situated below said straw walker assembly adjacent the rear portion thereof whereby a percentage of grain separated by said rear portion impinges upon said sensor tube, electrical transducer means in said sensor tube, responsive to the impingement of grain upon said sensor means, electrical amplifying means operatively connected to said last mentioned transducer means, and means operatively connecting said last mentioned amplifying means to said pulse generating circuit.

6. The device according to claim 3 which includes a further grain loss sensor component including a further sensor tube situated below said straw walker assembly adjacent the rear portion thereof whereby a percentage of grain separated by said rear portion impinges upon said further sensor tube, electrical transducer means in said further sensor tube, responsive to the impingement of grain upon said further sensor means, electrical amplifying means operatively connected to said last mentioned transducer means, and means operatively connecting said last mentioned amplifying means to said pulse generating circuit.

7. The device according to claim 4 which includes means to add the percentage of grain sensed by said first mentioned sensor component to the percentage of grain sensed by said second mentioned sensor component whereby the total grain loss is calculated by said measuring circuit.

8. The device according to claim 5 which includes means to add the percentage of grain sensed by said first mentioned sensor component to the percentage of grain sensed by said second mentioned sensor component whereby the total grain loss is calculated and displayed upon said indicating means.

9. The device according to claim 6 which includes means to add the percentage of grain sensed by said first mentioned sensor component to the percentage of grain sensed by said second mentioned sensor component whereby the total grain loss is calculated by said measuring circuit.

10. A method of measuring the grain loss by a combine or the like comprising the steps of constantly sampling a percentage of the grain passing over the rear end of the sieve component of the combine, electrically detecting the said percentage of grain in the form of pulses, calculating the total amount of grain passing over the rear end of the sieve from the percentage sample and displaying same in a read-out device, continually sampling a percentage of grain separated by the rear portion of the straw walker assembly of the combine, electrically detecting the said percentage of the grain in the form of pulses, calculating the total amount of grain separated by the rear portion of the straw walker from the said percentage sample and displaying same in a read-out device.

11. The method according to claim 10 which includes the additional step of adding the total amount of grain passing over the rear end of the sieve to the total amount of grain separated by the rear portion of the straw walker thereby monitoring on a continuous basis, the total amount of grain lost over the sieve component and straw walker assembly.

* * * * *